Figure 1:
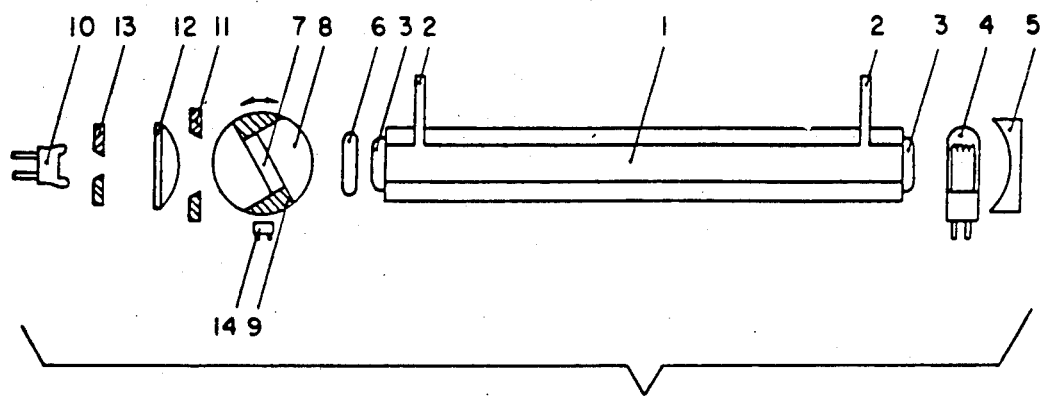

United States Patent [19]

Rantala et al.

[11] Patent Number: 5,070,245
[45] Date of Patent: Dec. 3, 1991

[54] APPARATUS AND METHOD FOR THE IDENTIFICATION OF GASES

[75] Inventors: Börje T. Rantala, Helsinki; Kurt P. Weckström, Esbo, both of Finland

[73] Assignee: Instrumentarium Corporation, Finland

[21] Appl. No.: 430,823

[22] Filed: Nov. 2, 1989

[30] Foreign Application Priority Data

Nov. 4, 1988 [FI] Finland .................................. 885115

[51] Int. Cl.⁵ .......................................... G01N 21/35
[52] U.S. Cl. ................................... 250/343; 250/339; 250/351
[58] Field of Search ...................... 250/351, 339, 343

[56] References Cited

U.S. PATENT DOCUMENTS

| | | | |
|---|---|---|---|
| 2,834,246 | 5/1958 | Foskett et al. | 356/418 |
| 3,914,055 | 10/1975 | Wolga et al. | 356/346 |
| 4,035,643 | 7/1977 | Barrett | 250/339 |
| 4,064,535 | 12/1977 | Cross et al. | 358/113 |
| 4,914,719 | 4/1990 | Conlon et al. | 250/339 |

FOREIGN PATENT DOCUMENTS

| | | | |
|---|---|---|---|
| 0254879 | 2/1988 | European Pat. Off. | 250/339 |
| 2948590 | 6/1981 | Fed. Rep. of Germany . | |
| 3021041 | 12/1981 | Fed. Rep. of Germany . | |
| 3334264 | 4/1984 | Fed. Rep. of Germany . | |
| 3736673 | 5/1989 | Fed. Rep. of Germany | 250/339 |
| 2148492 | 5/1985 | United Kingdom . | |
| 2163251 | 2/1986 | United Kingdom . | |

OTHER PUBLICATIONS

Aidan E. Roche and Alan M. Title, "Tilt Tunable Ultra Narrow-Band Filters for High Resolution Infrared Photometry." *Applied Optics*, vol. 14, No. 3 (Mar. 1975), pp. 765–770.

Primary Examiner—Constantine Hannaher
Attorney, Agent, or Firm—Andrus, Sceales, Starke & Sawall

[57] ABSTRACT

An apparatus and method for the identification of one or more anesthetic or other gases included in the respiratory air of a patient, said identification being effected within the infrared range 3–4 μm. The appratus comprises a radiation source (4), a chamber (1) for receiving therein a gas or gases to be examined, an optical filter (7) for passing the radiation exiting the chamber therethrough, an optical focusing device (12) through or via which the incoming radiation travels, a radiation detector (10) and a measuring processor (19) which performs the measuring and identification. The transmission band of the optical filter (7) or a combination of successive filters is within a range of 1.5%–0.4% of the mean transmission wavelength and the ray arriving at filter (7) has an angle of incidence between 10°–60°, the measuring effected within this range being performed at more than two angles. A measured spectrum is compared with a prior known spectrum by means of correlation algorithm to carry out the ientification. In a monitor for anesthetic gases, the content of gases is measured by means of a rapid-response sensor breath by breath. The quality or mixing ratio of an anesthetic gas is, in turn, measured by means of a slower sensor of the type described above.

25 Claims, 3 Drawing Sheets

APPARATUS AND METHOD FOR THE IDENTIFICATION OF GASES

The present invention relates to an apparatus intended for the identification of one or more anesthetic gases or other gases included in the respiratory air of a patient, said apparatus comprising a source of radiation, a chamber for feeding therein the gas or gases to be examined, an optical filter for passing the radiation therethrough, an optical focusing means through or via which the incoming radiation travels, and a radiation detector and a measuring processor which performs the identification. The invention relates also to a method for the identification of one or more anesthetic gases or other gases included in the respiratory air of a patient by means of infrared absorption as well as to an anesthetic gas monitor.

The basic equipment in any operating room includes a patient observation monitor. It can be used e.g. for controlling the contents of various components in the respiratory gas of a patient. The question is primarily about carbon dioxide and oxygen and in anesthesia cases about laughing gas and an anesthetic gas. The anesthetic gas is normally a halogenated hydrocarbon. The most common gases include halotane, enflurane and isoflurane. The requirements set on an anesthetic gas monitor include measuring speed, low noise, moderate size and price as well as ability to separate various gas types.

At present, the most important piece of equipment applicable to the separation of anesthetic gases is probably the mass spectrometer. However, it is a large and expensive apparatus which cannot be acquired in every hospital and which generally must be shared between several operating rooms.

Efforts have been made to utilize the Raman effect for the separation of gases. However, the spectral lines are extremely weak and thus it has been necessary to use powerful laser light for excitation. This results in a substantial increase to the price. Laser has nevertheless a poor stability of intensity due to the contamination of a measuring chamber provided inside the cavity.

Infrared absorption within the range of 7-14 $\mu$m has been utilized for the separation of anesthetic gases. Within this range, the absorption is quite substantial. The measuring is effected by using four channels, one of which is a reference. Each channel has usually been provided with its own filter and detector. The transmission band of a filter has usually been approximately 5% of the mean wavelength of transmission. Some idea of the signal proportions can be obtained on the basis of the presently used gases. The sensor is highly sensitive to environmental temperature changes due to a long wavelength. Modifications incurring high costs should be made in the measuring system in order to prevent thermal radiation. This system has not been capable of measuring within the range of 3 $\mu$m, wherein the disturbing thermal radiation would no longer be a problem because of the narrowness of the absorption spectrum of a hydrocarbon bond appearing even in anesthetic gases within this range.

Other problems in infrared absorption measurements have resulted from not obtaining reliable information about gas compositions even though pure gases can indeed be separated. More problems are caused by ethanol taken by a patient or administered to a patient for examination purposes, this being a rather serious source of trouble within the above-mentioned range.

As a physical phenomenon it is prior known that the transmission band of a narrow-band filter moves as a function of the angle of incidence (M. L. Baker and V. L. Yen, Appl. Opt. 6(1343)1967). It has generally been applied to the fine tuning of an interference filter. However, it has not been earlier used as an actual spectrometer because of a small measuring range.

A similar type of solution has been applied in a fiber-optical gas detector which is described in GB Patent 2163251B. In the cited patent the filter is not, however, used for storing and further analyzing the spectrum but primarily for detecting the background disturbances.

A problem in the operation of anesthetic gas monitors has also been the fact that up till now they have only measured the anesthetic gas content. Thus, the identification of an anesthetic gas, which is highly important aspect, must have been effected as a separate procedure. This has considerably increased the amount of work.

An object of this invention is to eliminate the above problems. An object of the invention is to provide a compact, simple, reliable and inexpensive apparatus for the identification of one or more anesthetic gases and other gases included in the respiratory air of a patient. Another object of the invention is to provide a method for the identification of one or more anesthetic gases or other gases included in the respiratory air of a patient. A further object of the invention is to provide an anesthetic gas monitor which performs both the content measuring and identification of an anesthetic gas.

The characterizing features of the invention are set forth in the annexed claims.

The operation of an apparatus of the invention suitable for the identification of one or more anesthetic gases or other gases, e.g. alcohol, included in the respiratory air of a patient, said apparatus being also possibly capable of measuring the gas content, is based on the dependence of the transmission of an interference filter upon the angle of incidence. A suitable range for the absorption spectrum is within the mean infrared range between 3-4 $\mu$m and particularly between 3-3.5 $\mu$m which includes the absorption spectrum of a hydrocarbon bond. The hydrocarbon spectrum of anesthetic gases lies within such a narrow range that an optical filter can be used for storing the spectrum. In this invention, every part of a spectrum has a major significance in the identification process of various gases. As the angle of incidence of infrared radiation changes, the peak of transmission shifts about 200 nm within said range. This is sufficient for storing this particular spectrum. The separating ability is primarily determined by the transmission band of an optical filter, which must be less than 1.5% of the mean transmission wavelength but nevertheless more than 0.4% of the mean transmission wavelength. With anesthetic gases below 0.4% the signal is already very weak and the separating ability is not any better, either. A preferred transmission band of the filter is approximately 0.5% of the mean transmission wavelength, i.e. in this case approximately 17 nm.

The identification is effected by means of a correlation algorithm which compares the measured spectrum to the prior known ones. This even facilitates the identification of the components in a gas composition. The addition of fresh gas into those to be identified is purely a practical procedure provided that there is characteristic absorption found within the spectral range. The identification can be allowed to be a relatively slow process compared to the measuring of a gas content. Thus, the measuring chamber may be large in volume, i.e. the chamber can be long for reaching a sufficient signal level. The output updating can be effected e.g. at one-second intervals.

Figure 3A:
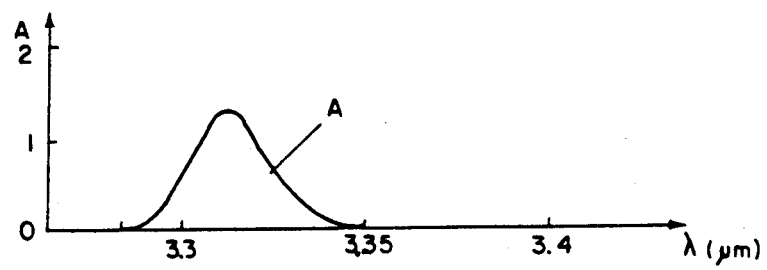
Figure 3B:
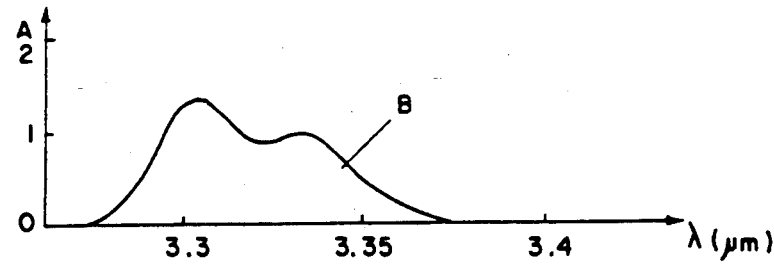
Figure 3C:
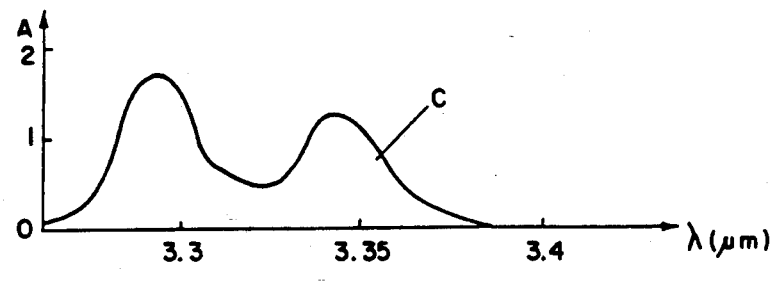
Figure 2:
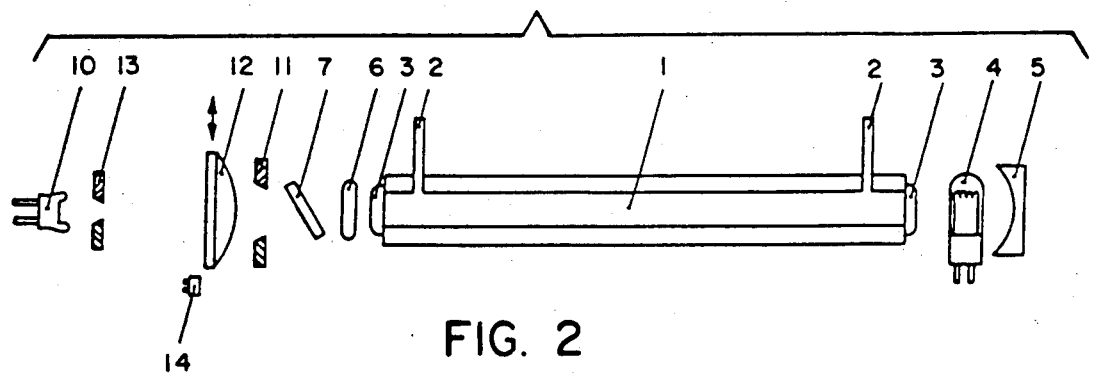
Figure 4:
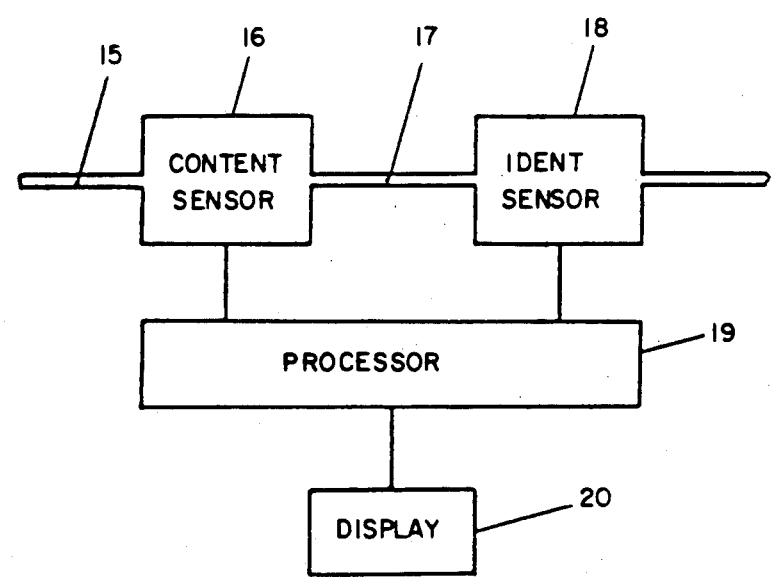
Figure 5:
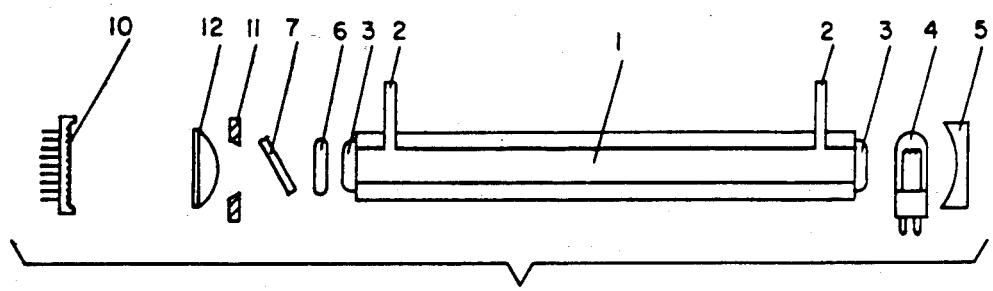
Figure 6:
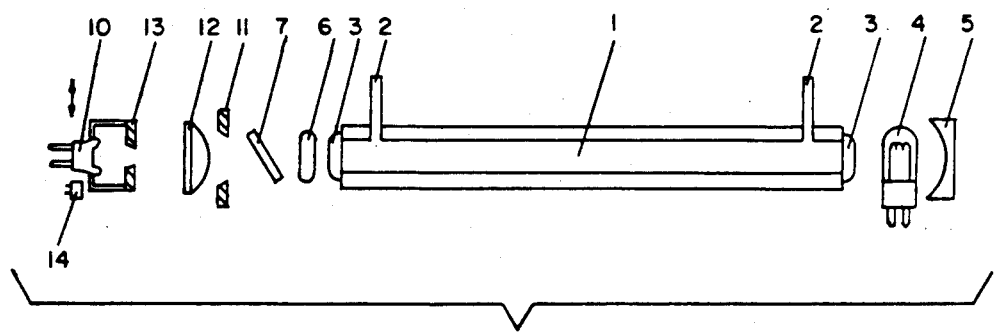
Figure 7:
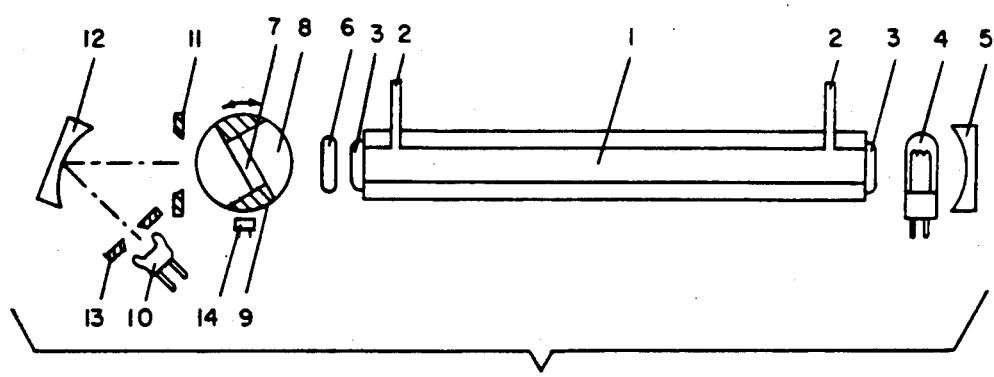

The invention will now be described in more detail with reference made to the accompanying drawings, in which FIG. 1 shows an apparatus of the invention for separating various gases, FIG. 2 shows an alternative apparatus of the invention for separating various gases, FIGS. 3a, 3b and 3c show the absorption spectra of three most common anesthetic gases, FIG. 4 shows a block diagram for the functions of an anesthetic gas monitor, FIG. 5 shows a modification of the apparatus of the present invention, FIG. 6 shows a further modification of the apparatus of the present invention having a movable detector, and FIG. 7 shows yet another modification of the apparatus of the present invention utilizing a concave mirror.

FIG. 1 illustrates an apparatus of this invention for the identification of various gases. This same apparatus can possibly be used also for measuring the gas contents. Into a measuring chamber 1 is supplied a sample of the respiratory gas of a patient through either one of the fittings 2. A suitable measuring chamber length is approximately 100 mm. The ends of the chamber is provided with windows 3 which have a good transmission over the desired wavelength range. Typically, the windows can be made of quartz or sapphire. A radiation source 4 is provided by an infrared lamp fitted with a quartz hood. The source could also be provided by using some other infrared source. A concave mirror 5 is used for reflecting radiation into the chamber in a manner that the proportion of penetrated parallel rays is optimized.

After traveling through the chamber, the rays pass next through a pre-filter 6, wherein the extra transmission zones of a measuring filter are removed. An optical filter 7, having a transmission band which is preferably 0.5% of the mean transmission wavelength, is mounted on a frame 8 rotating orthogonally to the optical axis. The filter can be rotated by a motor or inclined by some other means through a required angle which is appr. 10-60 degrees. The frame 8 is designed in a manner that the only way for the radiation to reach the detector is through filter 7 regardless of the angle thereof.

One end or possibly both ends of filter 7 is or are provided with a radiation non-permeable area 9 which is turned to block the path of radiation coming from the radiation source to prevent it from reaching a radiation detector 10. This characteristic is used for zeroing the apparatus.

The radiation coming through filter 7 is limited by means of an aperture 11 in a manner that the intensity of penetrated radiation depends as little as possible on the angle of a filter. The optical focusing means 12, preferably e.g. a convex lens, and a gap or slit 13 are used to select that parallel portion of the radiation which reaches detector 10. The optical focusing means 12 can be made of quartz or some other suitable optical material. Gap 13 is positioned on the focus level of optical means 12. The width and length of the gap are preferably selected so as to optimize the separating ability. If, for example, the band width of an employed filter 7 is 0.5% and the focus distance of an optical means is 25 mm, the gap may have a width of 1 mm and a length of 3 mm. The detector 10 may be e.g. a PbSe-detector, having a short rise time, but just as well employable is a pyroelectric detector or a thermocouple if the rate of change of the angle of filter 7 is low.

The signal level of detector 10 is regularly read into a measuring processor after a certain period from a triggering signal which in this case is provided e.g. by an opto-transceiver component 14 mounted in connection of the rotating frame. The entire spectrum could consist e.g. of 16 channels or measuring angles. In any case, the identification should be made at more than two angles. From the obtained infrared spectrum is subtracted a "zero spectrum" or the background which is obtained when measuring chamber 1 contains some known gas, such as air, which does not contain gases to be measured.

FIG. 2 illustrates an alternative apparatus of this invention for the separation of gases from each other. This apparatus comprises essentially the same components as that shown in FIG. 1. The radiation coming from a radiation source 4 is reflected by means of a concave mirror 5 into a gas-containing chamber 1 in a manner that the angular distribution of the penetrated rays is as uniform as possible within the range of +/−30 degrees. The wall of chamber 1 must be reflective of rays. The rays pass next through a pre-filter 6, as in FIG. 1. A narrow-band interference filter 7, having a transmission band which is preferably 0.5% of the mean transmission wavelength, is mounted in an inclined position relative to the optical axis, the angle of inclination being appr. 30°. By adjusting the angle of the filter, it is possible to effect the fine adjustment of the mid-point of the spectral range.

The radiation is limited by means of an aperture 11 preferably in a manner that the penetration in the plane of FIG. 2 is approximately +/−30° and orthogonally to the plane of the figure approximately +/−5°. An optical focusing means 12 and a gap 13 are used to select the parallel portion of radiation which reaches a detector 10. A linear shift of said optical focusing means 12 is used to select the angle of incidence for the parallel radiation penetrated through filter 7. Otherwise, the same aspects apply to gap 13 and optical means 12 as those reported in connection with FIG. 1.

The signal level of detector 10 is read as described in connection with FIG. 1. The difference in this case is that the opto-transceiver component 14 is mounted in connection with the shifting mechanism of optical means 12.

FIGS. 3a–3c illustrate the relative absorption of halotane (curve A in FIG. 3a), enflurane (curve B in FIG. 3b) and isoflurane (curve C in FIG. 3c) within the wavelength of 3–3.5 μm. The data collected in the memory of a processor can be used to build up a look-alike spectrum. Although the identification could be managed even visually by means of a suitable display unit, it is generally preferred to perform a correlative calculation between a measured spectrum and a master spectrum stored in the memory. This makes it possible to separate the components even from anesthetic gas compositions.

The correlation between a measured spectrum and a reference spectrum is described by a cross-correlation coefficient $$C = \sqrt{\frac{(N-2)(\Sigma xy)^2}{\Sigma x^2 \Sigma y^2 - (\Sigma xy)^2}},$$

wherein N is the number of observations or spectral points, x is a measured intensity at a certain point and y is a corresponding intensity of the reference spectrum. A high correlation coefficient indicates that the measured spectrum as a whole is similar to the reference spectrum and the identification is completed. A low correlation coefficient in comparison to all reference spectra indicates that the measured gas spectrum cannot be identified or that there is no absorbing gas.

The addition of a new gas to be identified is effected by adding its master spectrum into the memory and by making other necessary program-related changes. A possible thermal shift of the spectrum is also readily handled by calculation. By integrating across the spectrum it could be possible to acquire information about the content of a gas in question provided that first is effected a measuring without the absorption of anesthetic gas and with a high absorption (without radiation) for the determination of zero signal level. A possible spectrum shift due to temperature or a tolerance range of the transmission band of a filter does not affect the value of integral as long as the entire spectrum is small enough to fit inside the measuring range. A program-related correction is possible for correcting a possible non-linearity of the spectrum.

FIG. 4 illustrates a block diagram for the functions of an anesthetic gas monitor. The sampling is effected along a tube or tubing 15. A sensor 16 performs a rapid response measuring of the content of one or more anesthetic gases breath by breath. Such sensors are commercially available e.g. from Datex Instrumentarium Oy whose sensor is sold under the trade name ACX-100, so the operation of such sensors is not described in this context. Along a tube 17 the flow proceeds to a separate sensor 18, wherein the anesthetic gas is identified, i.e. its quality or mixing ratio is measured. A particularly suitable sensor 18 is shown in FIGS. 1 and 2 but other sensors can be used as well. This identification can be allowed to be slow as compared to the action of sensor 16. The measuring of a "zero spectrum" or the background occurs without disturbing the measuring activity of the content-measuring sensor 16. The obtained signals are processed in a measuring processor 19 and the results are shown on a display screen 20.

The invention is by no means limited to the described embodiments but various details of the invention can be modified within the scope of the annexed claims.

Instead of a single filter 7 it is of course possible to use a combination of successive filters mounted on the path of the same ray.

The shifting of optical focusing means 12 shown in FIG. 2 can be effected not only linearly but also by mounting a lens on the rim of a rotating disc.

The tiltable filter 7 or the movable optical means 12 appearing in FIGS. 1 and 2 could also be replaced with a stationary optical filter 7 and a stationary means 12 if the plane of focus is provided with an array of detectors 10, as shown in FIG. 5. It would be conceivable to mount e.g. 16 detectors in an array side by side. The detectors are read in an alternating fashion so as to provide a similar type of spectrum as the one above without the use of moving parts. An array of detectors could also be replaced with a single detector which would move in the plane of focus and read the signal level at desired channels, as shown in FIG. 6.

The pre-filtering glass 6, which appears in FIGS. 1 and 2, could also be positioned elsewhere in the optical path or even as the window of chamber 1. Often it is positioned as a component of filter 7.

FIGS. 1 and 2 show a lens as optical means 12. This lens could also be replaced e.g. with a concave mirror which would reflect the radiation to detector 10, as shown in FIG. 7. In the case of FIG. 1, the mirror could be fixedly mounted and, in the case of FIG. 2, it could be movable. In the case of FIG. 2, the mirror could also be fixedly mounted if the position of detector 10 can be shifted or if a plurality of adjacent detectors are used. Prior known are also other optical focusing means which would be suitable for use in apparatus of invention.

The gap 13 and detector 10 shown in FIGS. 1 and 2 could also be replaced with just a sufficiently small detector which would thus be only capable of detecting a radiation occurring within a certain wavelength range. Such a detector should preferably be linear.

The invention is by no means limited to any given configuration of components shown in the figures. It would be conceivable in FIG. 1, for example, that in the direction of radiation said filter 7 and gap 11 would be located upstream of measuring chamber 1. The same way, the pre-filtering glass 6 can be located upstream of chamber 1.

We claim:

1. Apparatus for the identification of one or more anesthetic or other gases included in the respiratory air of a patient, said apparatus comprising:
   a source of radiation (4);
   a chamber (1) for receiving the gas or gases to be examined and through which radiation from said source passes;
   an optical interference filter means (7) for receiving and transmitting radiation passing through said chamber, said optical interference filter means having a transmission band within a range of 1.5%–0.4% of the mean transmission wavelength of incoming radiation, said optical interference filter means receiving the radiation at an angle of incidence within a range of 10°–60°;
   optical focusing means (12) for the radiation transmitted by said optical interference filter means;
   a radiation detector (10) for receiving radiation from said optical focusing means; and
   measuring means (19) coupled to said radiation detector for analyzing the properties of the detected radiation obtained at more than two angles of incidence within said range of angles of incidence to identify the gas or gases.

2. An apparatus as set forth in claim 1, characterized in that the transmission band of said optical interference filter means (7) is approximately 0.5% the mean transmission wavelength.

3. An apparatus as set forth in claim 1, characterized in that the angle of said optical interference filter (7) can be changed relative to the incoming radiation for directing a certain wavelength band of the radiation to said detector (10).

4. An apparatus as set forth in claim 1, characterized in that the position of said optical focusing means (12) can be changed for directing a certain wavelength band of the radiation to said detector (10).

5. An apparatus as set forth in claim 1 characterized in that the position of both optical focusing means (12) and optical interference filter means (7) is stationary and wherein said radiation detector includes a detector (10) for each wavelength band to be detected.

6. An apparatus as set forth in claim 1 characterized in that the position of both optical focusing means (12) and optical interference filter means (7) is stationary, said radiation detector (10) being movable into alignment with a wavelength band to be detected.

7. An apparatus as set forth in claim 1, characterized in that said optical focusing means (12) is one of a lens and a mirror.

8. An apparatus as set forth in claim 7, characterized in that said optical focusing means is a lens and that the lens in convex.

9. An apparatus as set forth in claim 7, characterized in that said optical focusing means is a mirror and that the mirror is concave.

10. An apparatus as set forth in claim 1, characterized in that said source of radiation is an infrared radiation source.

11. An apparatus as set forth in claim 1, characterized in that said measuring means identifies the gas or gases spectrographically.

12. A method for the identification of one or more anesthetic or other gases included in the respiratory air of a patient, said method comprising the steps of:
passing infrared radiation through the respiratory air;
applying the radiation after it has passed through the respiratory air to an optical interference filter means at an angle of incidence within a range of 10°–60°, the transmission band of the optical interference filter means shifting, as a function of the angle of incidence through a range of 1.5%–0.4% of the mean transmission wavelength of the radiation;
focusing the radiation transmitted through the optical interference filter means;
detecting the focused radiation at more than two angles of incidence within said range of angles of incidence to obtain a measured spectrum of radiation properties; and
comparing the measured spectrum to a known spectrum to identify the gas or gases.

13. A method as set forth in claim 12, characterized as obtaining a measured spectrum within a range of 3–3.5 μm.

14. A method as set forth in claim 13 characterized in that from the measured spectrum is subtracted a background spectrum which is obtained in the absence of a gas to be identified.

15. A method as set forth in claim 12, characterized in that from the measured spectrum is subtracted a background spectrum which is obtained in the absence of a gas to be identified.

16. A monitor as set forth in claim 12 wherein said measuring means identifies the type of anesthetic gas spectrographically.

17. A monitor as set forth in claim 16 wherein said monitor is further defined as including means for enabling said measuring means to obtain a background spectrum omitting the gases to be identified without disturbing the determining action of said first sensor means.

18. A monitor for determining the amount at type of a anesthetic gas contained in the respiratory air of a patient, said monitor comprising:

a passageway along which the respiratory air of the patient flows;
first sensor means in communication with said passageway, said first sensor means having rapid response characteristics for determining the amount of anesthetic gas in the respiratory air on a breath by breath basis; and
second sensor means in communication with said passageway at a location downstream, in the flow direction of the respiratory air, from said first sensor means, said second sensor means having slower response characteristics than said first sensor means for identifying the type of anesthetic gas in the respiratory air from an accumulation of respiratory air obtained form a plurality of breaths of the patient.

19. A monitor according to claim 18 wherein said second sensor means comprises:
a source of infrared radiation;
a chamber for receiving and accumulating the respiratory air of the patient and through which radiation from said source passes;
an optical interference filter means for receiving and transmitting the radiation passing through said chamber, said optical interference filter means having a transmission band within a range of 1.5%–0.4% of the mean transmission wavelength of incoming radiation, said optical interference filter means receiving the radiation at an angle of incidence within a range of 10°60°;
optical focusing means for the radiation transmitted by said optical interference filter means;
a radiation detector for receiving radiation from said optical focusing means; and
measuring means coupled to said radiation detector for analyzing the properties of the detected radiation obtained at more than two angles of incidence within said range of angles of incidence to determine the type of anesthetic gas contained in the respiratory air of the patient.

20. A monitor as set forth in claim 18 wherein said second sensor means identifies the gas spectrographically, and wherein said monitor is further defined as including means for enabling said second sensor means to obtain a background spectrum omitting the gas to be identified without disturbing the determining action of said first sensor means.

21. A method for determining the amount and type of an anesthetic gas contained in the respiratory air of a patient, said method comprising the steps of:
passing the respiratory air of the patient along a flow path;
determining the amount of anesthetic gas in the respiratory air, said determination being carried out sufficiently rapidly as to enable same to be made on a breath by breath basis, said determination being carried out at a first point along the flow path; and
identifying the type of anesthetic gas in the respiratory air of the patient from an accumulation of respiratory air obtained from a plurality of breaths of the patient, said identification requiring a time period greater than that used to analyze respiratory air in an individual breath of the patient, said identification being carried out at a second point along the flow path downstream from the first point in the flow direction of the respiratory air.

22. A method as set forth in claim 21, characterized in that said step of identifying the type of anesthetic gas contained in the respiratory air of the patient includes the steps of:

passing infrared radiation through the respiratory air;

applying the radiation, after it has passed through the respiratory air, to an optical interference filter means at an angle of incidence within a range of 10°–60°, the transmission band of the optical interference filter means shifting, as a function of the angle of incidence through a range of 1.5%–0.4% of the mean transmission wavelength of incoming radiation;

detecting the radiation passed through the optical interference filter means to obtain a measured spectrum of radiation properties; and comparing the measured spectrum to a known spectrum to identify the anesthetic gas.

23. A method as set forth in claim 22 characterized as obtaining a measured spectrum within a range of 3–3.5 $\mu$.

24. A method as set forth in claim 23 characterized in that from the measured spectrum is subtracted a background spectrum which is obtained in the absence of a gas to be identified.

25. A method as set forth in claim 22 characterized in that from the measured spectrum is subtracted a background spectrum which is obtained in the absence of a gas to be identified.

* * * * *

UNITED STATES PATENT AND TRADEMARK OFFICE
CERTIFICATE OF CORRECTION

PATENT NO.  : 5,070,245
DATED       : December 3, 1991
INVENTOR(S) : Borje Rantala et al It is certified that error appears in the above-identified patent and that said Letters Patent is hereby corrected as shown below:

Claim 2, column 6, line 58       after "0.5%" insert ---of---

Claim 3, column 6, line 61       after "filter" insert ---means---

Claim 18, column 7, line 66,     delete "at" and substitute therefor ---and---

Claim 18, column 8, line 15,     delete "form" and substitute therefor ---from---

Claim 19, column 8, line 30,     delete "10°60°" and substitute therefor ---10° - 60°---

Signed and Sealed this

Thirty-first Day of August, 1993

Attest:

BRUCE LEHMAN

Attesting Officer

Commissioner of Patents and Trademarks